United States Patent
Lee (10) Patent No.: US 11,583,547 B2
(45) Date of Patent: Feb. 21, 2023

(54) CHEMOTHERAPY DRUG-SENSITIZING METHOD, AGENT COMPOSITION AND USE THEREOF

(71) Applicant: Shao-Chen Lee, New Taipei (TW)

(72) Inventor: Shao-Chen Lee, New Taipei (TW)

(73) Assignee: FU JEN CATHOLIC UNIVERSITY, New Taipei (TW)

( * ) Notice: Subject to any disclaimer, the term of this patent is extended or adjusted under 35 U.S.C. 154(b) by 107 days.

(21) Appl. No.: 17/239,318

(22) Filed: Apr. 23, 2021

(65) Prior Publication Data

US 2021/0386772 A1    Dec. 16, 2021

Related U.S. Application Data

(60) Provisional application No. 63/014,170, filed on Apr. 23, 2020.

(51) Int. Cl.
*A61K 31/7105* (2006.01)
*A61K 31/7068* (2006.01)

(52) U.S. Cl.
CPC ...... *A61K 31/7105* (2013.01); *A61K 31/7068* (2013.01)

(58) Field of Classification Search
None
See application file for complete search history.

(56) References Cited

PUBLICATIONS

Chen, Gang, et al. "MicroRNA-1976 functions as a tumor suppressor and serves as a prognostic indicator in non-small cell lung cancer by directly targeting PLCE1." Biochemical and biophysical research communications 473.4 (2016): 1144-1151.*

* cited by examiner

*Primary Examiner* — Patrick T Lewis
(74) *Attorney, Agent, or Firm* — Che-Yang Chen; Law Office of Michael Chen (57) ABSTRACT

A chemotherapy drug-sensitizing method includes: transfecting antisense oligonucleotide (e.g., siRNA-1976 or antagomir-1976) to a cancer cell to form a transfected cancer cell for blocking miR-1976 of the cancer cell; providing a treatment of cancer drug (or anticancer drug combination) to the transfected cancer cell whose miR-1976 is blocked by the antisense oligonucleotide; the transfected cancer cell providing a degree of sensitivity for the cancer drug due to its miR-1976 being blocked.

20 Claims, 5 Drawing Sheets
Specification includes a Sequence Listing.

CHEMOTHERAPY DRUG-SENSITIZING METHOD, AGENT COMPOSITION AND USE THEREOF

CROSS REFERENCE TO RELATED APPLICATIONS

This application claims priority to and the benefit of U.S. provisional patent application Ser. No. 63/014,170, filed Apr. 23, 2020, which is hereby incorporated by reference in its entirety.

SEQUENCE LISTING

This sequence listing is created on Aug. 26 2021 with the file name "SF21 0004UP Sequence Listing" and file size 1.03 KByte; the entire contents of which are hereby incorporated by reference.

BACKGROUND OF THE INVENTION

1. Field of the Invention

The present invention relates to a chemotherapy drug-sensitizing method, an agent composition thereof (or test reagent) and a method of use. Particularly, the present invention relates to a sensitivity enhancement of chemotherapy drug-sensitizing method, agent composition thereof (or test reagent) and method of use. More particularly, the present invention relates to the chemotherapy drug-sensitizing method, the agent composition thereof (or test reagent) and the method of use which utilizes inhibition of miR-1976 nucleic acids to sensitize chemotherapy drugs for cancers.

2. Description of the Related Art

Generally, human cancers includes brain cancer, nasopharyngeal cancer (NPC), oral cancer, laryngeal cancer, esophageal cancers stomach cancer, liver cancer, colorectal cancer, pancreatic cancer, lung cancer, breast cancer, prostate cancer, bladder cancer, cervical cancer, germ cell cancer, skin cancer, osteosarcoma cancer, blood cancer (including lymphoma cancer, leukemia and multiple myeloma), etc. By way of example, pancreatic cancer is one of most common type of cancers in the world. In 2017, an announcement of the ministry of health and welfare in Taiwan shows that malignant tumors is a top of ten major causes of death for recent years and pancreatic cancer is in sixth place of the causes of death. However, pancreatic cancer is most common in developed countries but prognosis of pancreatic cancer is usually quite poor with 1-year survival rate and 5-year survival rate merely reaching 25% and 5%. In some early detection cases, 5-year survival rate may increase to 20% but it cannot be effectively controlled for survival.

Furthermore, U.S. Pat. No. 8,969,315, entitled "ENHANCEMENT OF PLACENTAL STEM CELL POTENCY USING MODULATORY RNA MOLECULES," only discloses miR-1976 (i.e., microRNA-1976) and obviously does not teach an inhibition technique for miR-1976 nucleic acids and abilities of associated cancer cell apoptosis.

Another U.S. Patent Application Publication No. 2014/0080894, entitled "ENHANCED BIODISTRIBUTION OF OLGOMERS," only discloses miR-1976 (i.e., microRNA-1976) and obviously does not teach an inhibition technique for miR-1976 nucleic acids and abilities of associated cancer cell apoptosis.

Another U.S. Patent Application Publication No. 2018/0237772, entitled "HYBRID tRNA/pre-miRNA MOLECULES AND METHODS OF USE," only discloses miR-1976 (i.e., microRNA-1976) and obviously does not teach an inhibition technique for miR-1976 nucleic acids and abilities of associated cancer cell apoptosis.

Another U.S. Pat. No. 8,021,840, entitled "DIAGNOSTIC MARKER FOR INTERFERON RESPONSIVENESS IN MULTIPLE SCLEROSIS," only discloses XAF1 protein gene and obviously does not teach an inhibition technique for miR-1976 nucleic acids and abilities of associated cancer cell apoptosis.

Another U.S. Patent Application Publication No. 2007/0218493, entitled "DIAGNOSTIC MARKER FOR INTERFERON RESPONSIVENESS IN MULTIPLE SCLEROSIS," only discloses XAF1 protein gene and obviously does not teach an inhibition technique for miR-1976 nucleic acids and abilities of associated cancer cell apoptosis.

Another U.S. Patent Application Publication No. 2009/0215895, entitled "THERAPEUTIC AND CARRIER MOLECULES," only discloses XAF1 protein gene and obviously does not teach an inhibition technique for miR-1976 nucleic acids and abilities of associated cancer cell apoptosis.

Another U.S. Patent Application Publication No. 2017/0003277, entitled "BIOLOGICAL CHARACTERIZATION OF A GLATIRAMER ACETATE RELATED DRUG PRODUCT USING MAMMALIAN AND HUMAN CELLS," only discloses XAF1 protein gene and obviously does not teach an inhibition technique for miR-1976 nucleic acids and abilities of associated cancer cell apoptosis.

Another U.S. Patent Application Publication No. 2018/0369303, entitled "ONCOLYTIC RHABDOVIRUS," only discloses XAF1 protein gene and obviously does not teach an inhibition technique for miR-1976 nucleic acids and abilities of associated cancer cell apoptosis.

However, there is a need of providing an inhibition technique for miR-1976 nucleic acids and abilities of associated cancer cell apoptosis. The above-mentioned patents and patent application publications are incorporated herein by reference for purposes including, but not limited to, indicating the background of the present invention and illustrating the situation of the art.

SUMMARY OF THE INVENTION

The primary objective of this invention is to provide a chemotherapy drug-sensitizing method, an agent composition thereof (or test reagent) and a method of use. A cancer cell is transfected (or treated) to form a transfected cancer cell by antisense oligonucleotide (e.g., siRNA-1976 or antagomir-1976) for blocking miR-1976 of the cancer cell in future treatment. The transfected cancer cell is treated with a treatment of cancer drug (or anticancer drug combination) such that the miR-1976 of the transfected cancer cell is blocked by the antisense oligonucleotide. In the treatment of cancer drug, the transfected cancer cell provides an enhanced degree of sensitivity for the cancer drug due to its miR-1976 being blocked. Advantageously, the chemotherapy drug-sensitizing method, the agent composition (or test reagent) and the use of the present invention is successful in providing an enhanced degree of sensitivity of various cancer drugs.

The chemotherapy drug-sensitizing method in accordance with an aspect of the present invention includes:

transfecting antisense oligonucleotide (e.g., siRNA-1976 or antagomir-1976) to a cancer cell to form a transfected cancer cell for blocking miR-1976 of the cancer cell in future treatment;

providing a treatment of cancer drug (or anticancer drug combination) to the transfected cancer cell whose miR-1976 is blocked by the antisense oligonucleotide; and in a treatment of cancer drug, the transfected cancer cell providing an enhanced degree of sensitivity for the cancer drug due to the miR-1976 of cancer cell being blocked.

The chemotherapy drug-sensitizing method in accordance with an aspect of the present invention further includes:

searching at least one molecular target in the cancer cell;

screening at least one microRNA binding target within a predetermined cell;

providing a target binding RNA fragment to transcribe or derive into the microRNA binding target;

providing sequential analysis to the target binding RNA fragment and determining a target gene and a corresponding position thereof to obtain a plurality of miR-1976 binding targets; and seeking a XAF1 gene with the plurality of miR-1976 binding targets and providing an antisense oligonucleotide transfection procedure (e.g., siRNA-1976 or antagomir-1976 transfection procedure) to the cancer cell for blocking the miR-1976 of cancer cell.

In a separate aspect of the present invention, the at least one microRNA binding target is screened by specific gene cloning.

In a further separate aspect of the present invention, the target gene and the corresponding position thereof are obtained by blast analysis.

In yet a further separate aspect of the present invention, an expression of the miR-1976 obtained by micro array analysis or qPCR analysis.

The chemotherapy drug-sensitizing agent composition in accordance with an aspect of the present invention includes:

antisense oligonucleotide provided to treat a cancer cell with an antisense oligonucleotide transfection procedure (e.g., siRNA-1976 or antagomir-1976 transfection procedure) to thereby form a transfected cancer cell for blocking miR-1976 of the cancer cell in future treatment; and a cancer drug (or anticancer drug combination) provided to the transfected cancer cell performed as a sensitivity enhancement combination;

wherein the cancer drug is provided to treat the transfected cancer cell whose miR-1976 is blocked, with the miR-1976 blocked cancer cell providing an enhanced degree of sensitivity for the cancer drug.

In a separate aspect of the present invention, the sensitivity enhancement combination causes a reduction of miR-1976 in extracellular vesicle.

In a further separate aspect of the present invention, the sensitivity enhancement combination causes an increase of cancer cell death or a reduction of cancer cell growth.

In a further separate aspect of the present invention, the sensitivity enhancement combination causes an increase of cancer cell apoptosis marker.

In yet a further separate aspect of the present invention, the cancer cell apoptosis marker is selected from cleaved PARP.

In yet a further separate aspect of the present invention, the cancer cell apoptosis marker is corresponding to a XAF1 gene of the cancer cell.

The chemotherapy drug-sensitizing method in accordance with an aspect of the present invention includes:

transfecting antisense oligonucleotide (e.g., siRNA-1976 or antagomir-1976) to a pancreatic cancer cell to form a transfected pancreatic cancer cell for blocking miR-1976 of the pancreatic cancer cell in future treatment;

providing a treatment of pancreatic cancer drug (or anticancer drug combination) to the transfected pancreatic cancer cell whose miR-1976 is blocked by the antisense oligonucleotide; and in a treatment of pancreatic cancer drug, the transfected pancreatic cancer cell providing an enhanced degree of sensitivity for the pancreatic cancer drug due to the miR-1976 of pancreatic cancer cell being blocked.

The chemotherapy drug-sensitizing method in accordance with an aspect of the present invention further includes:

searching at least one molecular target in the pancreatic cancer cell;

screening at least one microRNA binding target within a predetermined pancreatic cell;

providing a target binding RNA fragment to transcribe or derive into the microRNA binding target;

providing sequential analysis to the target binding RNA fragment and determining a target gene and a corresponding position thereof to obtain a plurality of miR-1976 binding targets; and seeking a XAF1 gene with the plurality of miR-1976 binding targets and providing an antisense oligonucleotide transfection procedure (e.g., siRNA-1976 or antagomir-1976 transfection procedure) to the pancreatic cancer cell for blocking the miR-1976 of pancreatic cancer cell.

In a separate aspect of the present invention, the at least one microRNA binding target is screened by specific gene cloning.

In a further separate aspect of the present invention, the target gene and the corresponding position thereof are obtained by blast analysis.

In yet a further separate aspect of the present invention, an expression of the miR-1976 obtained by micro array analysis, qPCR analysis or RNA sequence analysis.

The chemotherapy drug-sensitizing agent composition in accordance with an aspect of the present invention includes:

antisense oligonucleotide provided to treat a pancreatic cancer cell with an antisense oligonucleotide transfection procedure (e.g., siRNA-1976 or antagomir-1976 transfection procedure) to thereby form a transfected pancreatic cancer cell for blocking miR-1976 of the pancreatic cancer cell in future treatment; and a pancreatic cancer drug (or anticancer drug combination) provided to the transfected pancreatic cancer cell performed as a sensitivity enhancement combination;

wherein the pancreatic cancer drug is provided to treat the transfected pancreatic cancer cell whose miR-1976 is blocked, with the miR-1976 blocked pancreatic cancer cell providing an enhanced degree of sensitivity for the pancreatic cancer drug.

In a separate aspect of the present invention, the sensitivity enhancement combination causes a reduction of miR-1976 in extracellular vesicle.

In a further separate aspect of the present invention, the sensitivity enhancement combination causes an increase of cancer cell death or a reduction of cancer cell growth.

In a further separate aspect of the present invention, the sensitivity enhancement combination causes an increase of pancreatic cancer cell apoptosis marker.

In yet a further separate aspect of the present invention, the pancreatic cancer cell apoptosis marker is selected from cleaved PARP.

In yet a further separate aspect of the present invention, the pancreatic cancer cell apoptosis marker is corresponding to a XAF1 gene of the cancer cell.

Further scope of the applicability of the present invention will become apparent from the detailed description given hereinafter. However, it should be understood that the detailed description and specific examples, while indicating preferred embodiments of the invention, are given by way of illustration only, since various will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

It is noted that a chemotherapy drug-sensitizing method, an agent composition thereof (or test reagent) and a method of use in accordance with the preferred embodiment of the present invention can be applicable to various cancers, including brain cancer, nasopharyngeal cancer (NPC), oral cancer, laryngeal cancer, esophageal cancers stomach cancer, liver cancer, colorectal cancer, pancreatic cancer, lung cancer, breast cancer, prostate cancer, bladder cancer, cervical cancer, germ cell cancer, skin cancer, osteosarcoma cancer, blood cancer (including lymphoma cancer, leukemia and multiple myeloma), which are not limitative of the present invention.

By way of example, a chemotherapy drug-sensitizing method, an agent composition thereof (or test reagent) and a method of use in accordance with another preferred embodiment of the present invention provide a chemotherapy drug sensitizer to enhance a degree of sensitivity for cancer drugs which can be used a lower dose prescription with an enhancement of curative effect in chemotherapy treatment.

By way of example, the chemotherapy drug-sensitizing method, agent composition thereof (or test reagent) and method of use in accordance with the preferred embodiment of the present invention are provided to block cell physiological effects of miR-1976 to achieve a sensitivity effect of cancer cells to chemotherapy drugs and to inhibit the growth of cancer cells. In addition, the microRNA is applied to screen molecular target of cells.

By way of example, the chemotherapy drug-sensitizing method, agent composition thereof (or test reagent) and method of use in accordance with the preferred embodiment of the present invention are provided with a technology of specific gene cloning. In addition, the chemotherapy drug-sensitizing method, agent composition thereof (or test reagent) and method of use in accordance with the preferred embodiment of the present invention are provided to form a test reagent for testing an amount of miR-1976 in blood samples after injecting a cancer drug.

Figure 1:
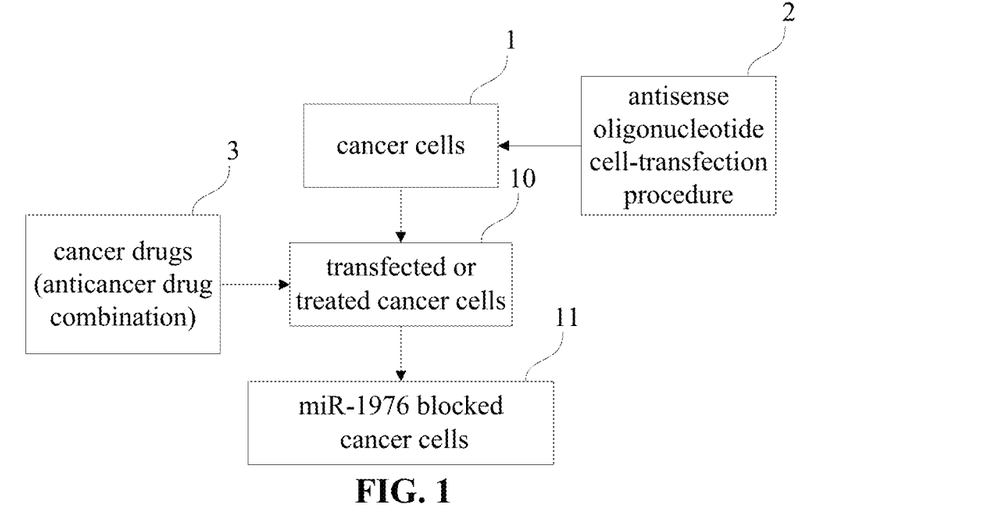
FIG. 1 is a flow chart of a chemotherapy drug-sensitizing method in accordance with a preferred embodiment of the present invention.

FIG. 1 shows a flow chart of a chemotherapy drug-sensitizing method in accordance with a preferred embodiment of the present invention. Referring now to FIG. 1, by way of example, the chemotherapy drug-sensitizing method in accordance with the preferred embodiment of the present invention includes:

transfecting antisense oligonucleotide (e.g., siRNA-1976 or antagomir-1976) to a cancer cell 1 (e.g., pancreatic cancer cell or other cancer cell), with an antisense oligonucleotide transfection procedure 2 (e.g., siRNA-1976 or antagomir-1976 transfection procedure), to form a transfected cancer cell 10 for blocking miR-1976 of the cancer cell 1 in future treatment;

providing a treatment of cancer drug (or anticancer drug combination) 3 to the transfected cancer cell 10 whose miR-1976 is blocked by the antisense oligonucleotide; and in a treatment of cancer drug, the transfected cancer cell 10 as a miR-1976 blocked cancer cell 11 providing an enhanced degree of sensitivity for the cancer drug 3 due to the miR-1976 of cancer cell 1 being blocked.

Still referring to FIG. 1, the chemotherapy drug-sensitizing method in accordance with an aspect of the present invention further includes:

searching at least one molecular target in the cancer cell 1;

screening at least one microRNA binding target within a predetermined cell;

providing a target binding RNA fragment to transcribe or derive into the microRNA binding target;

providing sequential analysis to the target binding RNA fragment and determining a target gene and a corresponding position thereof to obtain a plurality of miR-1976 binding targets; and seeking a XAF1 gene with the plurality of miR-1976 binding targets and providing the antisense oligonucleotide transfection procedure 2 (e.g., siRNA-1976 or antagomir-1976 transfection procedure) to the cancer cell 1 for blocking the miR-1976 of cancer cell 1.

With continued reference to FIG. 1, by way of example, in a preferred embodiment, the antisense oligonucleotide transfection procedure 2 includes a siRNA-1976 transfection procedure of pancreatic cancer (or other cancers) or an antagomir-1976 transfection procedure of pancreatic cancer (or other cancers).

With continued reference to FIG. 1, by way of example, in a preferred embodiment, the cancer drug (or anticancer drug combination) 3 is selected from various antimetabolites, including Methotrexate, Pemetrexed, Cytarabine, 5-Fluorouracil, Capecitabine, Gemcitabine, 6-Mercaptopurine, Azathioprine, Fludarabine, Cladribine, Hydroxyurea or the likes.

With continued reference to FIG. 1, by way of example, in another preferred embodiment, the cancer drug (or anticancer drug combination) 3 is selected from various alkylating agents, including Cyclophosphamide, Ifosfamide, Chlorambucil, Melphalan, Temozolomide, Carmustine, Lomustine, Streptozocin, Busulfan, Procarbazine, Cisplatin, Carboplatin, Oxaliplatin or the likes.

With continued reference to FIG. 1, by way of example, in another preferred embodiment, the cancer drug (or anticancer drug combination) 3 is selected from various topoisomerase inhibitors, including Irinotecan, Topotecan, Etoposide, Doxorubicin or the likes.

With continued reference to FIG. 1, by way of example, in another preferred embodiment, the cancer drug (or anticancer drug combination) 3 is selected from various mitotic inhibitors, including Vincristine, Vinblastine, Vinorelbine, Docetaxel, Paclitaxel, Eribulin, Ixabepilone, Epothilone or the likes.

With continued reference to FIG. 1, by way of example, in another preferred embodiment, the cancer drug (or anticancer drug combination) 3 is selected from various antitumor antibiotics, including Bleomycin, Actinomycin D, doxorubicin, daunorubicin, idarubicin, Mitomycin or the likes.

With continued reference to FIG. 1, by way of example, in another preferred embodiment, the cancer drug (or anticancer drug combination) 3 is selected from various protein kinase inhibitors, including Imatinib, Dasatinib, Nilotinib, Erlotinib, Gefitinib, Afatinib, Osimertinib, Alectinib, Crizotinib, Dabrafenib, Encorafenib, Vemurafenib, Trametinib, Ibrutinib, Ruxolitinib, Palbociclib or the likes.

With continued reference to FIG. 1, by way of example, in another preferred embodiment, the cancer drug (or anticancer drug combination) 3 is selected from various monoclonal antibody drugs against tumors or tumor receptors, or may be selected from L-asparaginase, Bortezomib, Carfilzomib, Ixazomib, Olaparib or the likes.

Figure 1A:
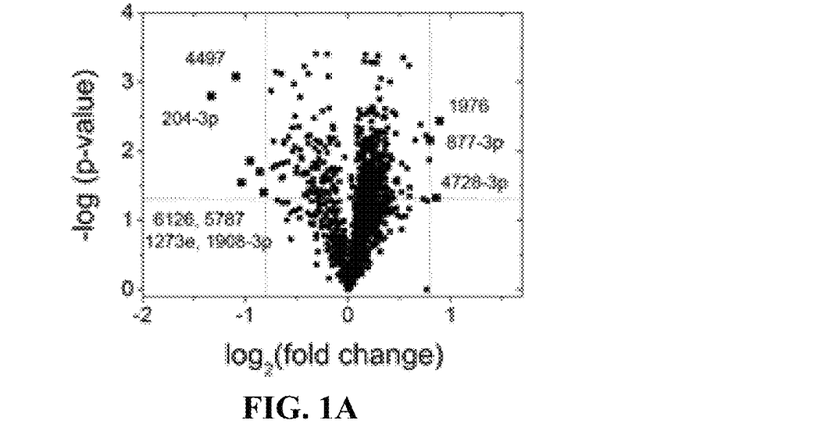
FIGS. 1A and 1B are microRNA expression charts released in extracellular vesicle and intracellular obtained from micro array analysis and qPCR analysis applied in the chemotherapy drug-sensitizing method in accordance with the preferred embodiment of the present invention.
Figure 1B:
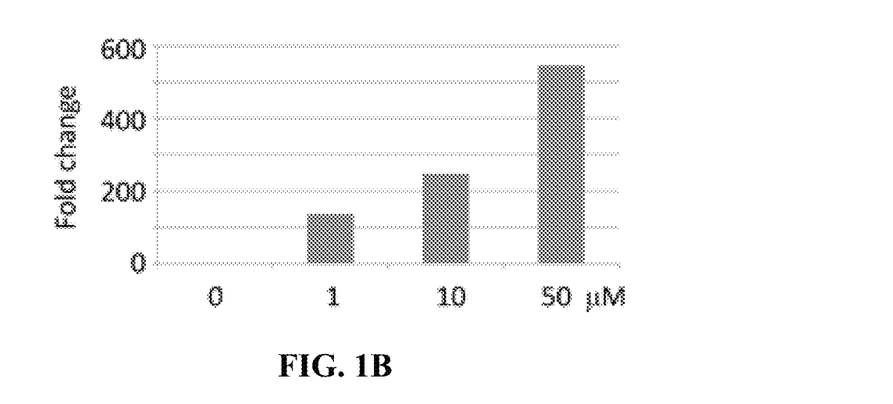

FIGS. 1A and 1B are microRNA expression charts released in extracellular vesicle and intracellular obtained from micro array analysis and qPCR analysis applied in the chemotherapy drug-sensitizing method in accordance with the preferred embodiment of the present invention. Referring now to FIGS. 1A and 1B, by way of example, the qPCR analysis shows highest increases of miR-1976, miR-877-3p and miR-4728-3p in pancreatic cancer cells, with showing an obvious increase of miR-1976.

Turning now to FIG. 1B, by way of example, an amount of miR-1976 in pancreatic cancer cells can be selectively increased by induction of gemcitabine which may damage the pancreatic cancer cells.

Figure 2A:
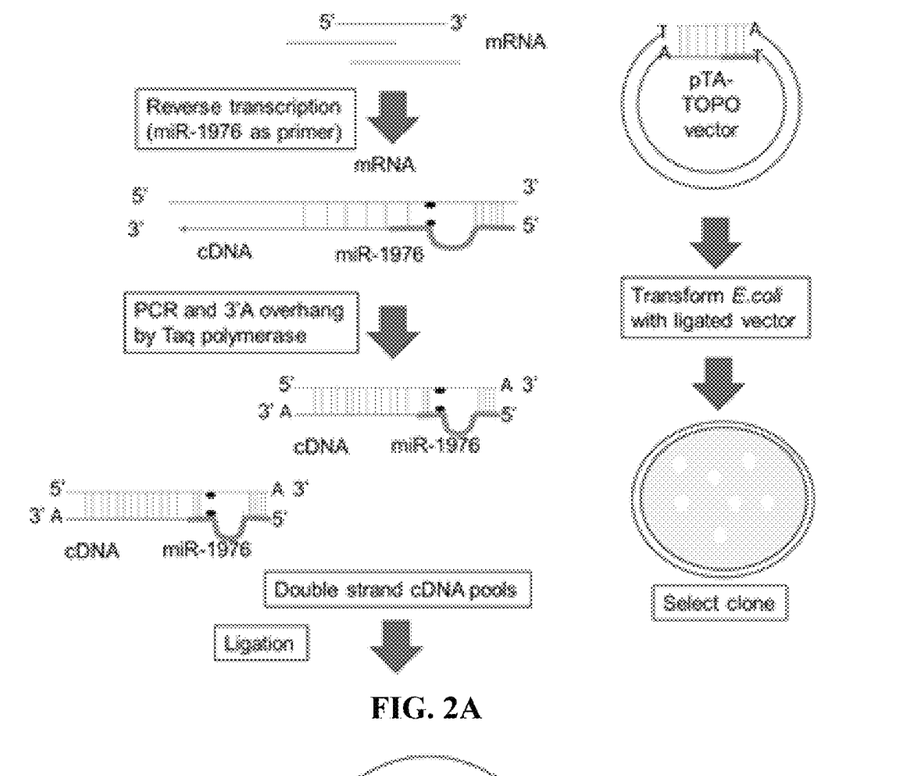
FIGS. 2A and 2B are miR-1976 binding target chart obtained from specific gene cloning and potential target gene (relating to cancer cell apoptosis) chart compared with bioinformatics (XAF1) applied in the chemotherapy drug-sensitizing method in accordance with the preferred embodiment of the present invention.
Figure 2B:
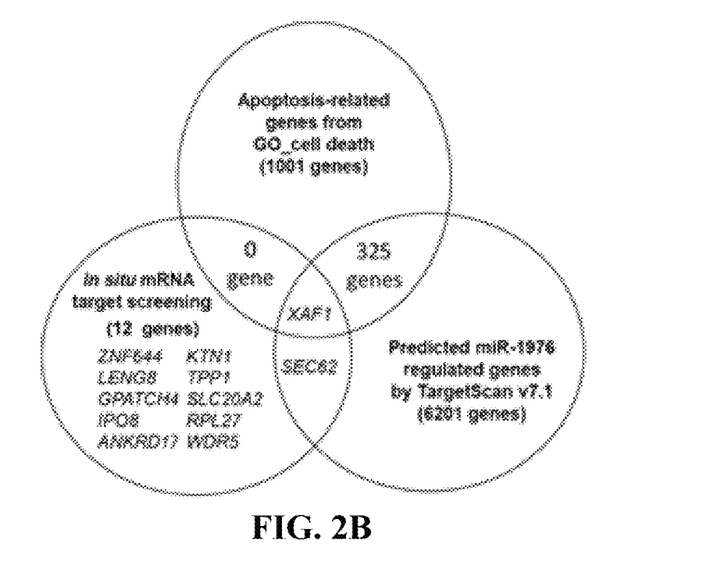

FIGS. 2A and 2B are miR-1976 binding target chart obtained from specific gene cloning and potential target gene (relating to cancer cell apoptosis) chart compared with bioinformatics (XAF1) applied in the chemotherapy drug-sensitizing method in accordance with the preferred embodiment of the present invention. Referring now to FIGS. 2A and 2B, by way of example, the chemotherapy drug-sensitizing method in accordance with the preferred embodiment of the present invention includes: screening at least one microRNA binding target within a predetermined cell with a specific gene cloning technology; providing a target binding RNA fragment to transcribe or derive into the microRNA binding target; providing sequential analysis to the target binding RNA fragment and determining a target gene and a corresponding position thereof with blast analysis to obtain a plurality of miR-1976 binding targets; comparing and seeking a cell apoptosis gene or a related gene with the plurality of miR-1976 binding targets and predicting miR-1976 targets with a tool of targetscan to obtain a XAF1 gene or a related gene which is a control target of miR-1976.

Figure 3A:
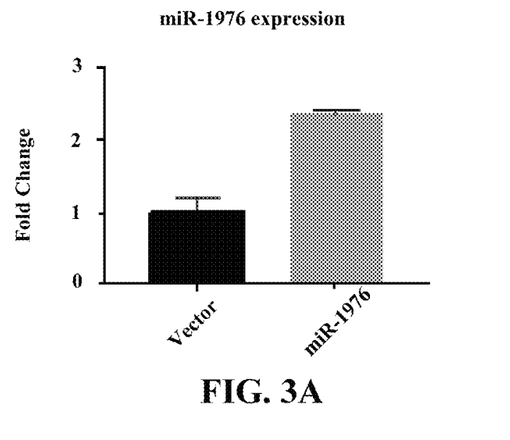
FIGS. 3A to 3C are miR-1976 expression charts obtained from qPCR analysis and western blot analysis applied in the chemotherapy drug-sensitizing method in accordance with the preferred embodiment of the present invention.
Figure 3B:
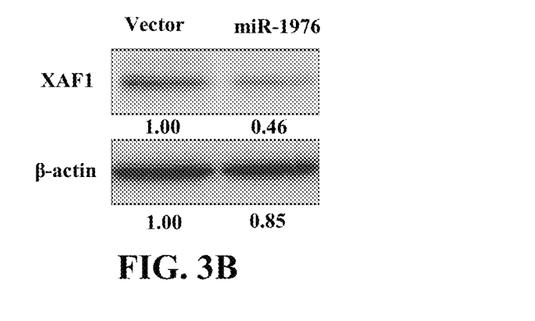
Figure 3C:
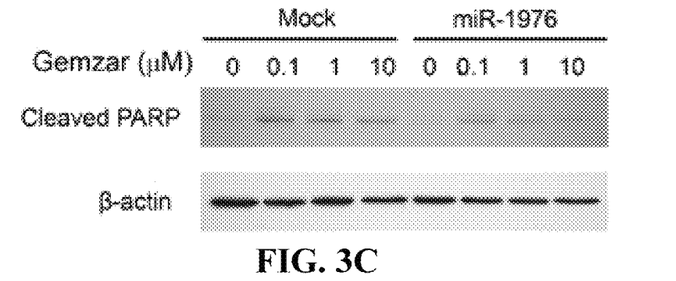

FIGS. 3A to 3C are miR-1976 expression charts obtained from qPCR analysis and western blot analysis applied in the chemotherapy drug-sensitizing method in accordance with the preferred embodiment of the present invention. Referring now to FIGS. 3A to 3C, by way of example, the chemotherapy drug-sensitizing method in accordance with the present invention provides a greater amount of miR-1976 expression in cancer cells as a simulation of cell damage to cause an increase of miR-1976 or cells affected by an effect of extracellular vesicles containing miR-1976. Obviously, when a greater amount of miR-1976 expression is shown in cancer cells, an amount of XAF1 is relatively reduced and an amount of pancreatic cancer cell apoptosis marker (i.e., cleaved PARP) is specifically reduced as well.

Figure 4A:
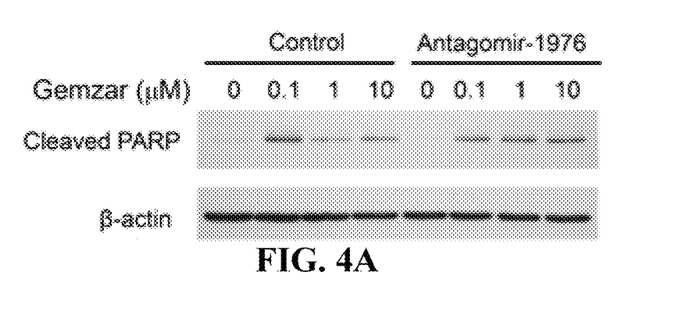
FIGS. 4A and 4B are cell apoptosis charts of BxPC-3 and AsPC-1 pancreatic cancer cells with antagomiR-1976 transfection obtained from western blot analysis applied in the chemotherapy drug-sensitizing method in accordance with the preferred embodiment of the present invention.
Figure 4B:
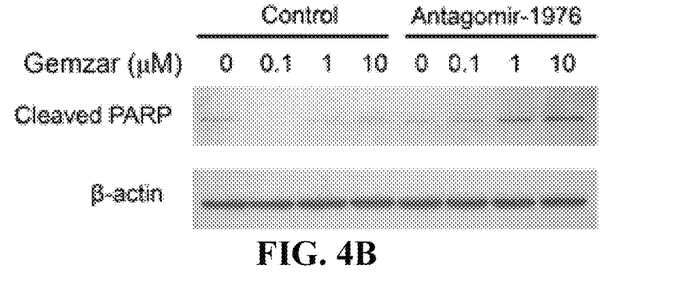
Figure 5A:
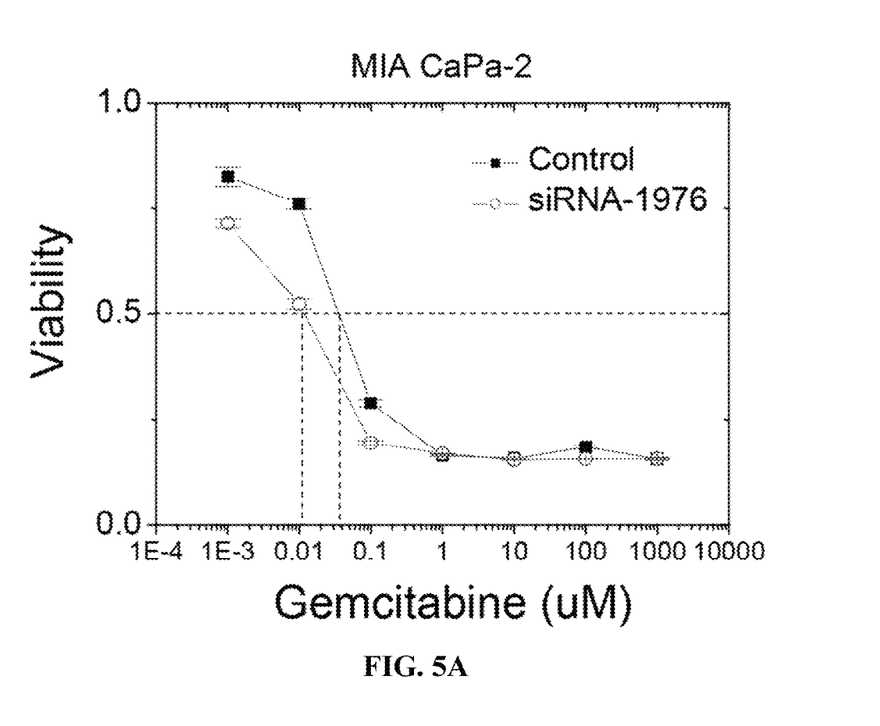
FIGS. 5A to 5D are cancer cell viability charts of MIA Capa-2, BxPC-3 and AsPC-1 pancreatic cancer cells with siRNA-1976 transfection applied in the chemotherapy drug-sensitizing method in accordance with the preferred embodiment of the present invention.
Figure 5B:
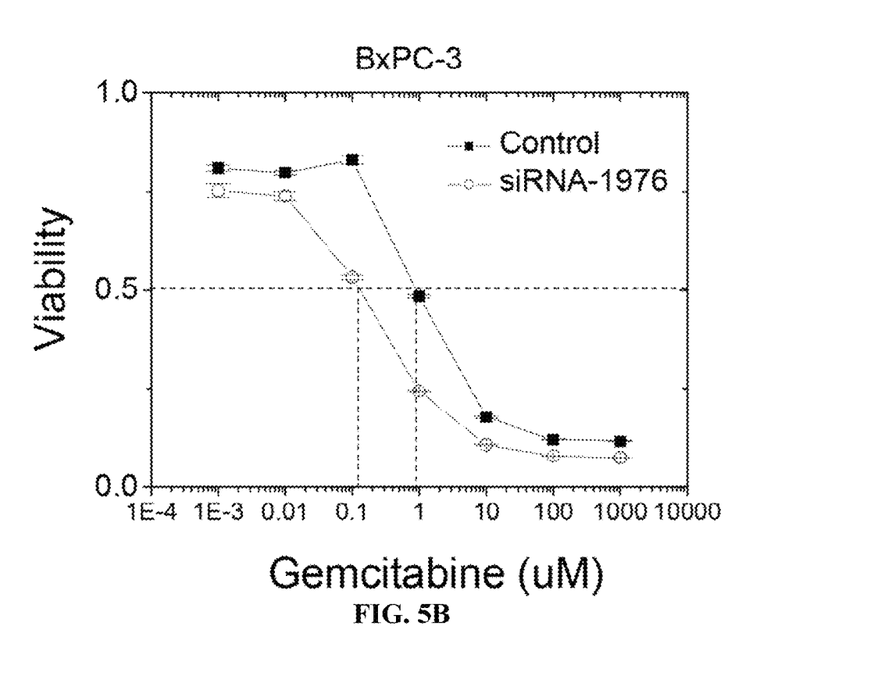
Figure 5C:
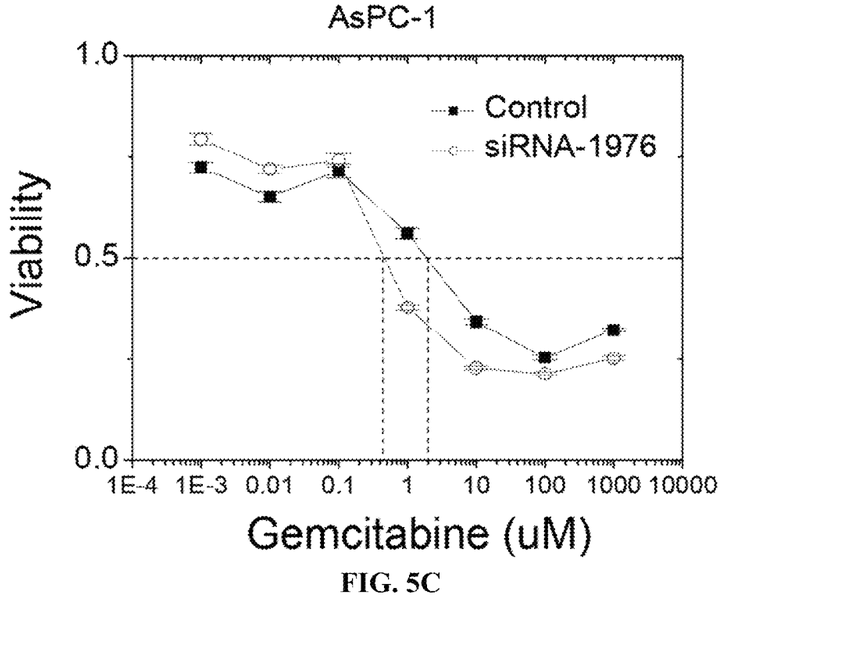
Figure 5D:
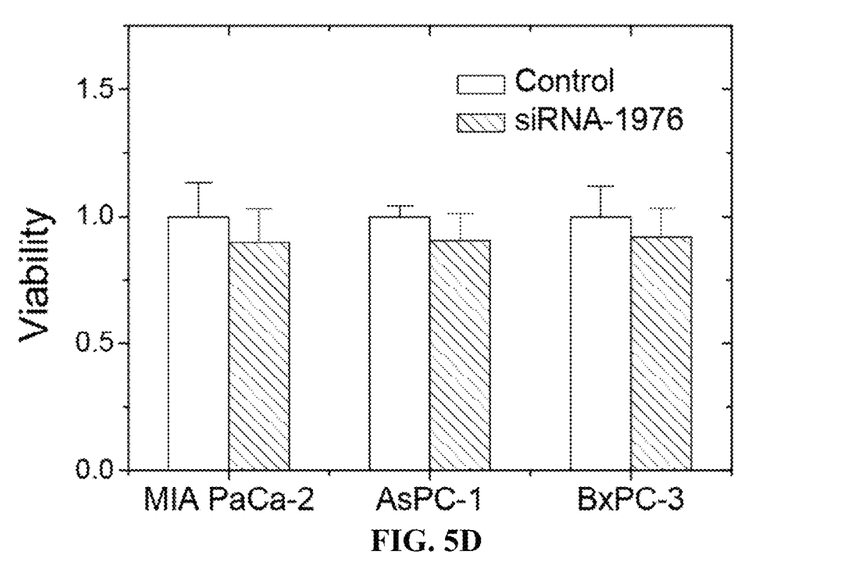

FIGS. 4A and 4B are cell apoptosis charts of BxPC-3 and AsPC-1 pancreatic cancer cells with antagomiR-1976 transfection obtained from western blot analysis applied in the chemotherapy drug-sensitizing method in accordance with the preferred embodiment of the present invention. Referring now to FIG. 4A, by way of example, results of pancreatic cancer cell BxPC-3 applied in the chemotherapy drug-sensitizing method in accordance with the present invention are shown. Referring now to FIG. 4B, by way of example, results of pancreatic cancer cell AsPC-1 applied in the chemotherapy drug-sensitizing method in accordance with the present invention are shown.

Still referring to FIGS. 4A and 4B, by way of example, an amount of pancreatic cancer cell apoptosis marker (i.e., cleaved PARP) of transfected pancreatic cancer cells is obviously increased due to the miR-1976 of pancreatic cancer cells being blocked.

By way of example, the chemotherapy drug-sensitizing method in accordance with a preferred embodiment of the present invention can replace an antagomir-1976 inhibitor with a miR-1976 inhibitor or an equivalent inhibitor.

By way of example, the antagomir used herein in the preferred embodiment of the present invention has a specific structure to form a small interfering RNA (siRNA) molecule which has a specific RNA sequence as a specific sequence of "ACAGCAA".

By way of example, the antagomir-1976 used herein in the preferred embodiment of the present invention has a 20-nt RNA sequence as a specific sequence of 5'-ACAGCAAGGAGGGCAGGAGG-3'.

By way of example, the antagomir-1976 used herein in another preferred embodiment of the present invention has a key area which is applied to inhibit nucleotide-1976, with the key area including a specific sequence of "ACAGCAA" which has a nucleotide length of 17-42 nucleobase.

By way of example, the antagomir-1976 used herein in another preferred embodiment of the present invention has a miR-1976 inhibitor sequence of 5'-(N)xACAGCAA(N)y, where N is nucleobase A, U, G or C; x is 0 to 5; and y is 10 to 30.

cells if only chemotherapy drug-sensitizing agent composition is applied in chemotherapy treatment without using any chemotherapy drug.

Although the invention has been described in detail with reference to its presently preferred embodiment, it will be understood by one of ordinary skills in the art that various modifications can be made without departing from the spirit and the scope of the invention, as set forth in the appended claims.

SEQUENCE LISTING

```
<160> NUMBER OF SEQ ID NOS: 3

<210> SEQ ID NO 1
<211> LENGTH: 7
<212> TYPE: RNA
<213> ORGANISM: Unknown
<220> FEATURE:
<223> OTHER INFORMATION: antagomir

<400> SEQUENCE: 1 acagcaa                                                              7

<210> SEQ ID NO 2
<211> LENGTH: 20
<212> TYPE: RNA
<213> ORGANISM: Unknown
<220> FEATURE:
<223> OTHER INFORMATION: antagomir-1976

<400> SEQUENCE: 2
acagcaagga gggcaggagg                                               20

<210> SEQ ID NO 3
<211> LENGTH: 9
<212> TYPE: RNA
<213> ORGANISM: Unknown
<220> FEATURE:
<223> OTHER INFORMATION: antagomir-1976
<220> FEATURE:
<221> NAME/KEY: misc_feature
<222> LOCATION: (1)..(1)
<223> OTHER INFORMATION: n is nucleobase A, U, G or C, and the number of
      n is 0 to 5
<220> FEATURE:
<221> NAME/KEY: misc_feature
<222> LOCATION: (9)..(9)
<223> OTHER INFORMATION: n is nucleobase A, U, G or C, and the number of
      n is 10 to 30

<400> SEQUENCE: 3 nacagcaan                                                            9
```

FIGS. 5A to 5D are cancer cell viability charts of MIA Capa-2, BxPC-3 and AsPC-1 pancreatic cancer cells with siRNA-1976 transfection applied in the chemotherapy drug-sensitizing method in accordance with the preferred embodiment of the present invention. Referring now to FIGS. 5A to 5D, by way of example, the chemotherapy drug-sensitizing method in accordance with the present invention must use at least one chemotherapy drug-sensitizing agent composition (e.g., siRNA-1976 or equivalent drug-sensitizing composition) and at least one chemotherapy drug, thereby affecting viability of pancreatic cancer cells.

With continued reference to FIGS. 5A to 5D, the chemotherapy drug-sensitizing method in accordance with the present invention cannot affect viability of pancreatic cancer

What is claimed is:

1. A chemotherapy drug-sensitizing method comprising:
transfecting antagomir-1976 to a cancer cell to form a transfected cancer cell for blocking miR-1976 of the cancer cell in future treatment; and
providing a treatment of cancer drug combination to the transfected cancer cell and the transfected cancer cell providing an enhanced degree of sensitivity for the cancer drug combination.

2. The chemotherapy drug-sensitizing method as defined in claim 1 further comprising:
searching at least one molecular target in the cancer cell;
screening at least one microRNA binding target within a predetermined cell;

providing a target binding RNA fragment to transcribe or derive into the microRNA binding target;

providing sequential analysis to the target binding RNA fragment and determining a target gene and a corresponding position thereof to obtain a plurality of miR-1976 binding targets; and seeking a XAF1 gene with the plurality of miR-1976 binding targets and providing an antisense oligonucleotide transfection procedure to the cancer cell for blocking the miR-1976 of cancer cell.

3. The chemotherapy drug-sensitizing method as defined in claim 2, wherein the microRNA binding target is screened by specific gene cloning.

4. The chemotherapy drug-sensitizing method as defined in claim 2, wherein the target gene and the corresponding position thereof are obtained by blast analysis.

5. The chemotherapy drug-sensitizing method as defined in claim 2, wherein an expression of the miR-1976 obtained by qPCR analysis.

6. A chemotherapy drug-sensitizing agent composition comprising:

antagomir-1976, provided to treat a cancer cell with an antagomir-1976 transfection procedure to thereby form a transfected cancer cell for blocking miR-1976 of the cancer cell; and a cancer drug combination, provided to the transfected cancer cell performed as a sensitivity enhancement combination;

wherein the cancer drug combination is provided to treat the transfected cancer cell, with the cancer cell providing an enhanced degree of sensitivity for the cancer drug combination.

7. The chemotherapy drug-sensitizing agent composition as defined in claim 6, wherein the sensitivity enhancement combination causes a reduction of miR-1976 in extracellular vesicle.

8. The chemotherapy drug-sensitizing agent composition as defined in claim 6, wherein the sensitivity enhancement combination causes an increase of cancer cell apoptosis marker.

9. The chemotherapy drug-sensitizing agent composition as defined in claim 8, wherein the cancer cell apoptosis marker is selected from cleaved PARP.

10. The chemotherapy drug-sensitizing agent composition as defined in claim 8, wherein the cancer cell apoptosis marker is corresponding to a XAF1 gene of the cancer cell.

11. A chemotherapy drug-sensitizing method for pancreatic cancer comprising:

transfecting antagomir-1976 to a pancreatic cancer cell to form a transfected pancreatic cancer cell for blocking miR-1976 of the pancreatic cancer cell in future treatment; and providing a treatment of pancreatic cancer drug combination to the transfected pancreatic cancer cell and the transfected pancreatic cancer cell providing an enhanced degree of sensitivity for the pancreatic cancer drug combination.

12. The chemotherapy drug-sensitizing method for pancreatic cancer as defined in claim 11 further comprising:

searching at least one molecular target in the pancreatic cancer cell;

screening at least one microRNA binding target within a predetermined cell;

providing a target binding RNA fragment to transcribe or derive into the microRNA binding target;

providing sequential analysis to the target binding RNA fragment and determining a target gene and a corresponding position thereof to obtain a plurality of miR-1976 binding targets; and seeking a XAF1 gene with the plurality of miR-1976 binding targets and providing an antisense oligonucleotide transfection procedure to the pancreatic cancer cell for blocking the miR-1976 of pancreatic cancer cell.

13. The chemotherapy drug-sensitizing method for pancreatic cancer as defined in claim 12, wherein the microRNA binding target is screened by specific gene cloning.

14. The chemotherapy drug-sensitizing method for pancreatic cancer as defined in claim 12, wherein the target gene and the corresponding position thereof are obtained by blast analysis.

15. The chemotherapy drug-sensitizing method for pancreatic cancer as defined in claim 12, wherein an expression of the miR-1976 obtained by qPCR analysis.

16. A chemotherapy drug-sensitizing agent composition for pancreatic cancer comprising:

antagomir-1976, provided to treat a pancreatic cancer cell with an antagomir-1976 transfection procedure to thereby form a transfected pancreatic cancer cell for blocking miR-1976 of the cancer cell; and a pancreatic cancer drug combination, provided to the transfected pancreatic cancer cell performed as a sensitivity enhancement combination;

wherein the pancreatic cancer drug combination is provided to treat the transfected pancreatic cancer cell, with the pancreatic cancer cell providing an enhanced degree of sensitivity for the pancreatic cancer drug combination.

17. The chemotherapy drug-sensitizing agent composition for pancreatic cancer as defined in claim 16, wherein the sensitivity enhancement combination causes a reduction of miR-1976 in extracellular vesicle.

18. The chemotherapy drug-sensitizing agent composition for pancreatic cancer as defined in claim 16, wherein the sensitivity enhancement combination causes an increase of pancreatic cancer cell apoptosis marker.

19. The chemotherapy drug-sensitizing agent composition for pancreatic cancer as defined in claim 18, wherein the pancreatic cancer cell apoptosis marker is selected from cleaved PARP.

20. The chemotherapy drug-sensitizing agent composition for pancreatic cancer as defined in claim 18, wherein the pancreatic cancer cell apoptosis marker is corresponding to a XAF1 gene of the pancreatic cancer cell.

* * * * *